US00PP14843P3

(12) United States Plant Patent
Hasegawa

(10) Patent No.: US PP14,843 P3
(45) Date of Patent: Jun. 1, 2004

(54) HYBRID CARNATION PLANT NAMED 'CFPC SARI'

(50) Latin Name: *Dianthus caryophyllus*
Varietal Denomination: CFPC SARI

(75) Inventor: Oscar T. Hasegawa, Salinas, CA (US)

(73) Assignee: California Florida Plant Company, L.P., Salinas, CA (US)

( * ) Notice: Subject to any disclaimer, the term of this patent is extended or adjusted under 35 U.S.C. 154(b) by 0 days.

(21) Appl. No.: 10/208,168

(22) Filed: Jul. 29, 2002

(65) Prior Publication Data

US 2004/0019940 P1 Jan. 29, 2004

(51) Int. Cl.[7] ..... A01H 5/00
(52) U.S. Cl. ..... Plt./273
(58) Field of Search ..... Plt./273

*Primary Examiner*—Anne Marie Grunberg
*Assistant Examiner*—Susan B. McCormick
(74) *Attorney, Agent, or Firm*—Christie, Parker & Hale, LLP

(57) ABSTRACT

A new variety of carnation plant producing attractive yellow picotee purple flowers.

1 Drawing Sheet

Classification: The present invention relates to a new Hybrid *Dianthus caryophyllus* plant.

Variety denomination: The new plant has the varietal denomination 'CFPC SARI'.

BACKGROUND OF THE INVENTION

The present invention relates to a new and distinct variety of carnation plant which was originated by me by crossing as the female parent the variety known as 'CFPC LACY' (U.S. Plant Pat. No. 11,884) and as the male parent an undistributed and unpatented seedling identified as '970111'. The varietal denomination of the new variety is 'CFPC SARI'.

SUMMARY OF THE INVENTION

Among the novel characteristics possessed by the new variety which distinguish it from other varieties of which of I am aware, are its attractive yellow picotee purple flowers which retain color without fading. When grown in a greenhouse in Salinas, Calif., in 4½ inch plastic pots, plants are about 8½ inches tall and about 5 inches in diameter. Flower diameter averages about 2 inches with a crown of about ¾ inch (average). Foliage is about 3 inches long and about ¼ inch wide at its widest point.

Asexual reproduction by propagation by cuttings of the new variety as performed in Salinas, Calif., shows that the foregoing and other distinguishing characteristics come true to form and are established and transmitted through succeeding propagation.

COMPARISON WITH PARENT

The new variety differs from its parents in flowers that possess a unique color pattern of light purple picotee on yellow background. The parents do have this flower coloration.

BRIEF DESCRIPTION OF ILLUSTRATION

The accompanying illustration shows typical specimens of the vegetative growth and flowers of the new variety depicted in color as nearly true as it is reasonably possible to make the same in color illustration of this character.

DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypical expression may vary depending upon varying environmental, seasonal and cultural conditions.

The information provided herein is based on observations of 110-day-old plants grown inside commercial greenhouses at Salinas, Calif. The height of plant and flower and foliage size are established as an average using standard commercial cultural practices.

Classification:
- *Botanical.*—Hybrid *Dianthus caryophyllus.*
- *Commercial.*—Carnation, standard disbud, greenhouse type, suitable for cut flower production and as a pot spray.

Plant:
- *Height.*—About 8½ inches.
- *Form.*—Herbaceous.
- *Growing habit.*—Semi-upright.
- *Blooming habit.*—As a spray (pot).
- *Blooming season.*—Year round.
- *Rooting time/habit.*—About 18 days.
- *Breaking action.*—Good.
- *Mutation prone.*—No.
- *Disease resistance.*—Good, resistence to soil-borne diseases such as *Fusarium oxysporum,* and *F. graminearum* and root-rots such as damping off, water molds and the like as is typical of carnations.
- *Temperature tolerance.*—Wide range.

Foliage (base of plant):
- *Color.*—Upper side: Near 147A. Lower side: Near 137A.
- *Size.*—About 3 inches long and about ¼ inch wide.
- *Quantity.*—Numerous.

*Shape.*—Lanceolate.

*Texture.*—Smooth.

*Ribs.*—Central keel.

*Arrangement.*—Bi-lateral along stem.

*Stem.*—Size: Stem diameter 3/16 inch. Color: Near 139A.

*Bud.*—Shape: Ovoid. Color: Near 143C. Length: About 1 1/16 inches. Diameter: About 3/8 inch.

*Calyx.*—Sepals: About 5. Length: About 5/16 inch. Width: About 1/4 inch. Color Outside: Near 144A. Inside: Near 147D.

*Leaf base and apex.*—Leaf base posseses a smooth edge, color near 138D; leaf apex possesses a smooth edge, color near 147A.

Bloom:

*Shape.*—Rounded.

*Size.*—Diameter: About 2 inches. Depth: About 3/4 inch.

*Borne.*—As a spray.

*Color.*—Petal edge color of near 80A in continuous picotee pattern of about 1/32 inch width with occasional spot near 80A and fine radial lines on a background of near 4D. General tonality: Yellow and purple. Upper side: Near 4D. Lower side: Near 4D. Center: Near 4D. Outer petals: Near 80A.

*Permanence.*—Dry up on receptacle.

*Keeping quality.*—Very good.

*Fragrance.*—Strong perfume.

Petalage:

*Quantity.*—About 24.

*Outer petal size.*—Length: About 1 3/4 inches. Width: About 1 1/8 inches.

*Central petal size.*—Length: About 1 5/8 inches. Width: About 15/16 inch.

*Texture.*—Smooth.

*Appearance.*—Shiny.

*Form.*—Fan shaped, margin finely serrated.

Reproductive organs:

*Stamen.*—None.

*Anthers.*—None.

*Filaments.*—None.

*Pistil.*—1. Length: About 1 1/8 inches. Color: Whiter than 155D.

*Stigma.*—2. Color: Near 4D.

*Fertility.*—Male: Sterile. Female: Good.

*Ovary.*—Shape: Conical. Color Base: Near 155D. Body: Near 144C. Apex: Near 144C.

*Fruit.*—No seed or fruit produced.

I claim:

1. A new and distinct carnation plant of the variety substantially as herein shown and described.

* * * * *

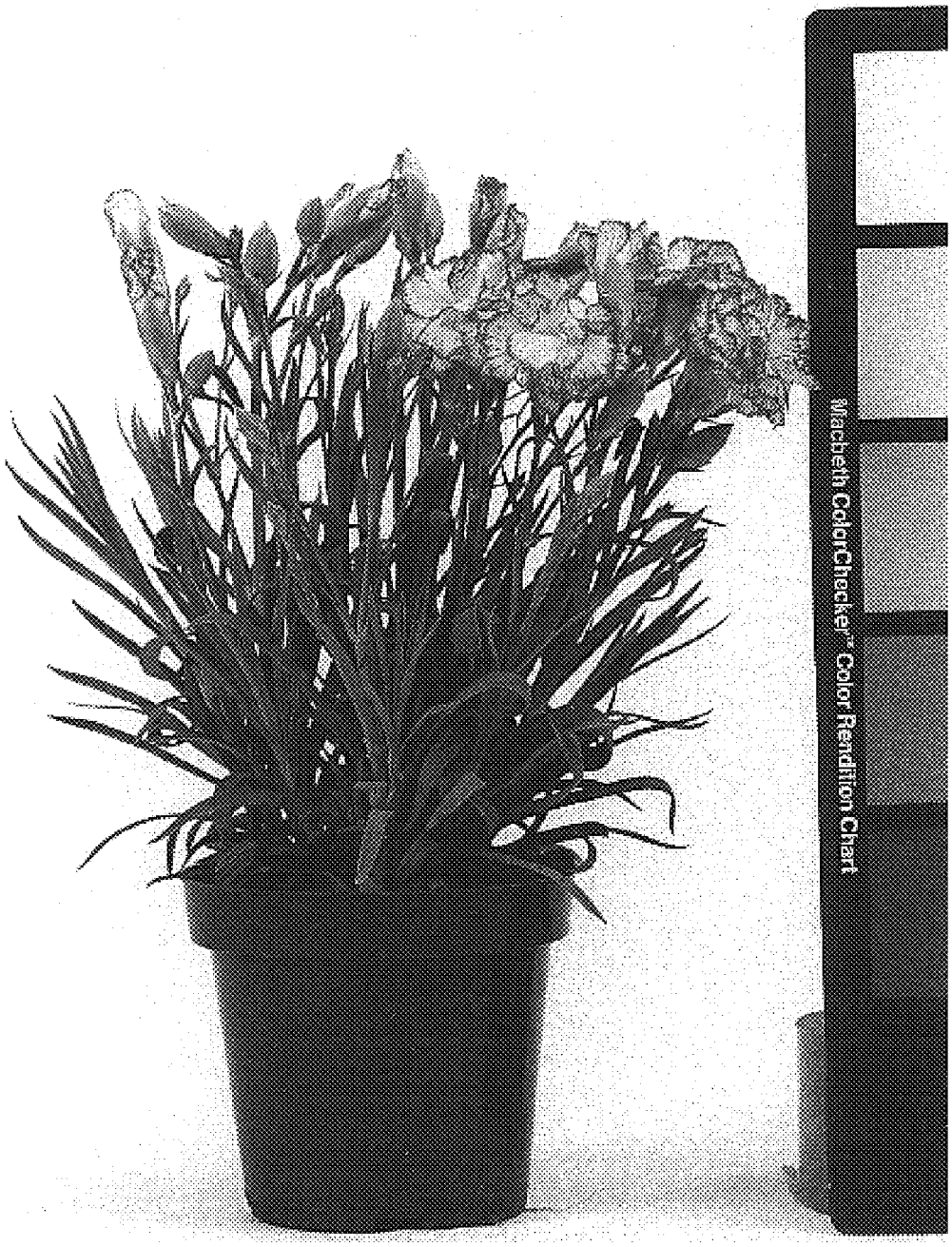
Macbeth ColorChecker™ Color Rendition Chart